US012564581B2

(12) United States Patent
Brown et al.

(10) Patent No.: US 12,564,581 B2
(45) Date of Patent: Mar. 3, 2026

(54) PYRAZOLE PHARMACEUTICAL COMPOSITION

(71) Applicant: Intervet Inc., Madison, NJ (US)

(72) Inventors: Chad D. Brown, Pittstown, NJ (US); Christopher D. Kulczar, Jersey City, NJ (US); Chen-Chao Wang, West Windsor, NJ (US); Michelle H. Fung, Watchung, NJ (US)

(73) Assignee: Intervet Inc., Rahway, NJ (US)

( * ) Notice: Subject to any disclaimer, the term of this patent is extended or adjusted under 35 U.S.C. 154(b) by 858 days.

(21) Appl. No.: 17/785,671

(22) PCT Filed: Dec. 18, 2020

(86) PCT No.: PCT/EP2020/086944
§ 371 (c)(1),
(2) Date: Jun. 15, 2022

(87) PCT Pub. No.: WO2021/123108
PCT Pub. Date: Jun. 24, 2021

(65) Prior Publication Data
US 2023/0070369 A1 Mar. 9, 2023

Related U.S. Application Data

(60) Provisional application No. 62/951,185, filed on Dec. 20, 2019.

(51) Int. Cl.

| | |
|---|---|
| *A61K 31/4439* | (2006.01) |
| *A61K 9/20* | (2006.01) |
| *A61P 17/00* | (2006.01) |

(52) U.S. Cl.
CPC ........ *A61K 31/4439* (2013.01); *A61K 9/2013* (2013.01); *A61K 9/2031* (2013.01); *A61K 9/2054* (2013.01); *A61K 9/2059* (2013.01); *A61K 9/2095* (2013.01); *A61P 17/00* (2018.01)

(58) Field of Classification Search
CPC .............. A61K 31/4439; A61K 9/2013; A61K 9/2054; A61K 31/4155
See application file for complete search history.

(56) References Cited

U.S. PATENT DOCUMENTS

| | | | |
|---|---|---|---|
| 5,891,469 | A | 4/1999 | Amselem |
| 10,022,373 | B2 | 7/2018 | Wan |
| 10,875,847 | B2 | 12/2020 | Fuller et al. |
| 2013/0243853 | A1 | 9/2013 | Tefferi et al. |

(Continued)

FOREIGN PATENT DOCUMENTS

| | | |
|---|---|---|
| CN | 101031284 A | 9/2007 |
| CN | 102499929 A | 6/2012 |
| CN | 103237544 A | 8/2013 |

(Continued)

OTHER PUBLICATIONS

Handbook of Pharmaceutical Excipients, 6th Ed, 2009, pp. 317-322, 663-666 (Year: 2009).*

(Continued)

*Primary Examiner* — San Ming R Hui
(74) *Attorney, Agent, or Firm* — David J. Kerwick

(57) ABSTRACT

A pharmaceutical composition of pyrazole compound and a surfactant and a method of using the same to treat atopic dermatitis.

25 Claims, 3 Drawing Sheets

(56) References Cited

U.S. PATENT DOCUMENTS

| | | | |
|---|---|---|---|
| 2014/0378490 | A1 | 12/2014 | Wu et al. |
| 2015/0141351 | A1 | 5/2015 | Durak et al. |

FOREIGN PATENT DOCUMENTS

| | | | |
|---|---|---|---|
| CN | 110062754 | A | 7/2019 |
| WO | 1998008490 | A1 | 3/1998 |
| WO | 2006036614 | A2 | 4/2006 |
| WO | 2006039268 | A2 | 4/2006 |
| WO | 2006119498 | A2 | 11/2006 |
| WO | 2013041042 | A1 | 3/2013 |
| WO | 2018108969 | A1 | 6/2018 |
| WO | 2019122068 | A1 | 6/2019 |

OTHER PUBLICATIONS

Harskamp et al., Immunology of Atopic Dermatitis: Novel Insights into Mechanisms and Immunomodulatory Therapies, Seminars in Cutaneous Medicine and Surgery, 2013, 132-139, 32.

Hill, P.B., Development of an owner-assessed scale to measure the severity of pruritus in dogs, Veterinary Dermatology, 2007, 301-308, 18.

Nuttall et al., Canine Atopic Dermatitis—what have we learned?, Veterinary Record, 2013, 201-207, 172(8).

Olivry, Thierry, Validation of the Canine Atopic Dermatitis Extent and Severity Index (CADESI)-4, a simplified severity scale for assessing skin lesions of atopic dermatitis in dogs, Veterinary Dermatology, 2014, 77-e25, 25.

Rahman et al., The Pathology and Immunology of Atopic Dermatitis, Inflammation & Allergy—Drug Targets, 2011, 486-496, 10.

Florence, Alexander T. et al., Physicochemical Principles of Pharmacy, Pharmaceutical Press, 4th Ed., (1.4 + 1.4.1), 19-23, 2006.

Khoruzhaya, T.G. et al., The Fifth Pharmaceutical Factor: Dosage Form and Route of Administration, Biopharmacy is a Scientific Direction in the Development and Improvement of Medicines: A Scholar Manual, N/A, 11-13, 2006 (English translation).

Kondratieva, T.S., Biopharmaceutics as the Theoretical Basis for Drug Formulation Technology, Drug Formulation Technology, vol. 2, 36, 37, 74, 76 + 111, 1991 (English translation).

Mashkovsky, M.D., Medicines, M.: Novaya Volna, 16th Edition, 8, 12+13, 2012 (English translation).

Sutyagain, V.M. et al., Chemistry and Physics of Polymers: A Scholar Manual, Chemistry and Physics of Polymers: A Scholar Manual, N/A, 132, 140, 151 + 173, 2003 (English translation).

Verbeeck, R.K. et al., Generic substitution: The use of medicinal products containing different salts and implications for safety and efficacy, European Journal of Pharmaceutical Sciences, 28, 1-6, 2006.

Yang, Conglian et al., Recent Advances in the Application of Vitamin E TPGS for Drug Delivery, Theranostics, 8 (2), 464-485, 2018.

Jin, Feiyan et al., Tabletability assessment of conventional formulations containing Vitamin E tocopheryl polyethylene glycol succinate, International Journal of Pharmaceutics, 389, 58-65, 2010.

Ma, Jianfend et al., Effect of down-regulation of SRGN gene on apoptosis and JAK/STAT signaling pathway in breast cancer cells, Oncol Prog, 16(6), 698-701, 2018.

* cited by examiner

PYRAZOLE PHARMACEUTICAL COMPOSITION

CROSS-REFERENCE TO RELATED APPLICATIONS

This application is a national stage entry under 35 U.S.C. § 371 of PCT/EP2020/086944 filed Dec. 18, 2020, which claims priority to U.S. application 62/951,185 filed Dec. 20, 2019, the contents of which are hereby incorporated by reference in their entireties.

BACKGROUND

WO 2018/108969 discloses compounds of formula I which are selective Janus kinase (JAK) inhibitors, and as such are useful for the treatment of JAK-mediated diseases such as atopic dermatitis, arthritis, and cancer. Specifically, 1-[(3R,4S)-4-cyanotetrahydropyran-3-yl]-3-[(2-fluoro-6-methoxy-4-pyridyl)amino]pyrazole-4-carboxamide (I) is disclosed.

Formula (I)

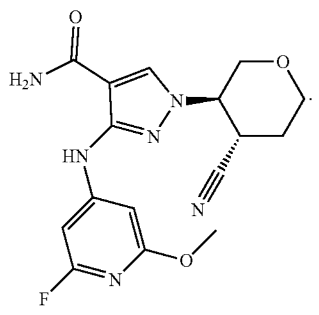

In a cIL-31 induced pruritus study, the compound of Formula (I) significantly suppressed pruritus with respect to placebo and in a similar magnitude to oclacitinib (Apoquel®). Apoquel® is a commercially available product for the treatment of atopic dermatitis in dogs. Also disclosed are methods of treating atopic dermatitis by oral administration of compound (I).

WO 2013/041042 discloses pyrazole carboxamides as Janus kinase inhibitors that are useful for the treatment of rheumatoid arthritis, asthma, chronic obstructive pulmonary disease (COPD) and cancer. The compounds of this disclosure are of the following formula.

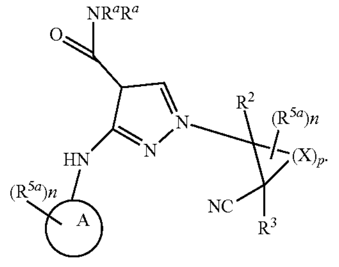

Atopic dermatitis (AD) is a relapsing pruritic and chronic inflammatory skin disease, that is characterized by immune system dysregulation and epidermal barrier abnormalities in humans. The pathological and immunological attributes of atopic dermatitis have been the subject of extensive investigations [reviewed in Rahman et al. *Inflammation & Allergy-drug target* 10:486-496 (2011) and Harskamp et al., *Seminar in Cutaneous Medicine and Surgery* 32:132-139 (2013)]. Atopic dermatitis is also a common condition in companion animals, especially dogs, where its prevalence has been estimated to be approximately 10-15% of the canine population. The pathogenesis of atopic dermatitis in dogs and cats [reviewed in Nuttall et al., *Veterinary Records* 172(8):201-207 (2013)] shows significant similarities to that of atopic dermatitis in man including skin infiltration by a variety of immune cells and $CD4^+$ Th2 polarized cytokine milieu including the preponderance of IL-4, IL-13, and IL-31. In addition, IL-22 has been implicated in the exaggerated epithelial proliferation leading to epidermal hyperplasia that is characteristic of atopic dermatitis.

Applicants have found that the inclusion of the surfactant D-$\alpha$-ocopheryl polyethylene glycol 1000 succinate (TPGS) in formulations of the compound of Formula (I) resulted in improved bioavailability of the compound of Formula (I) when compared to formulations without TPGS.

SUMMARY OF THE INVENTION

An embodiment of the invention is a pharmaceutical composition comprising a pharmaceutically effective amount of 1-[(3R,4S)-4-cyanotetrahydropyran-3-yl]-3-[(2-fluoro-6-methoxy-4-pyridyl)amino]pyrazole-4-carboxamide and a surfactant of an ester of a tocopherol, a polyethylene glycol (PEG) and a dicarboxylic acid.

Another embodiment of the invention is a method of treating atopic dermatitis comprising orally administering to an animal in need of an effective amount of the above pharmaceutical composition.

DETAILED DESCRIPTION

Figure 1:
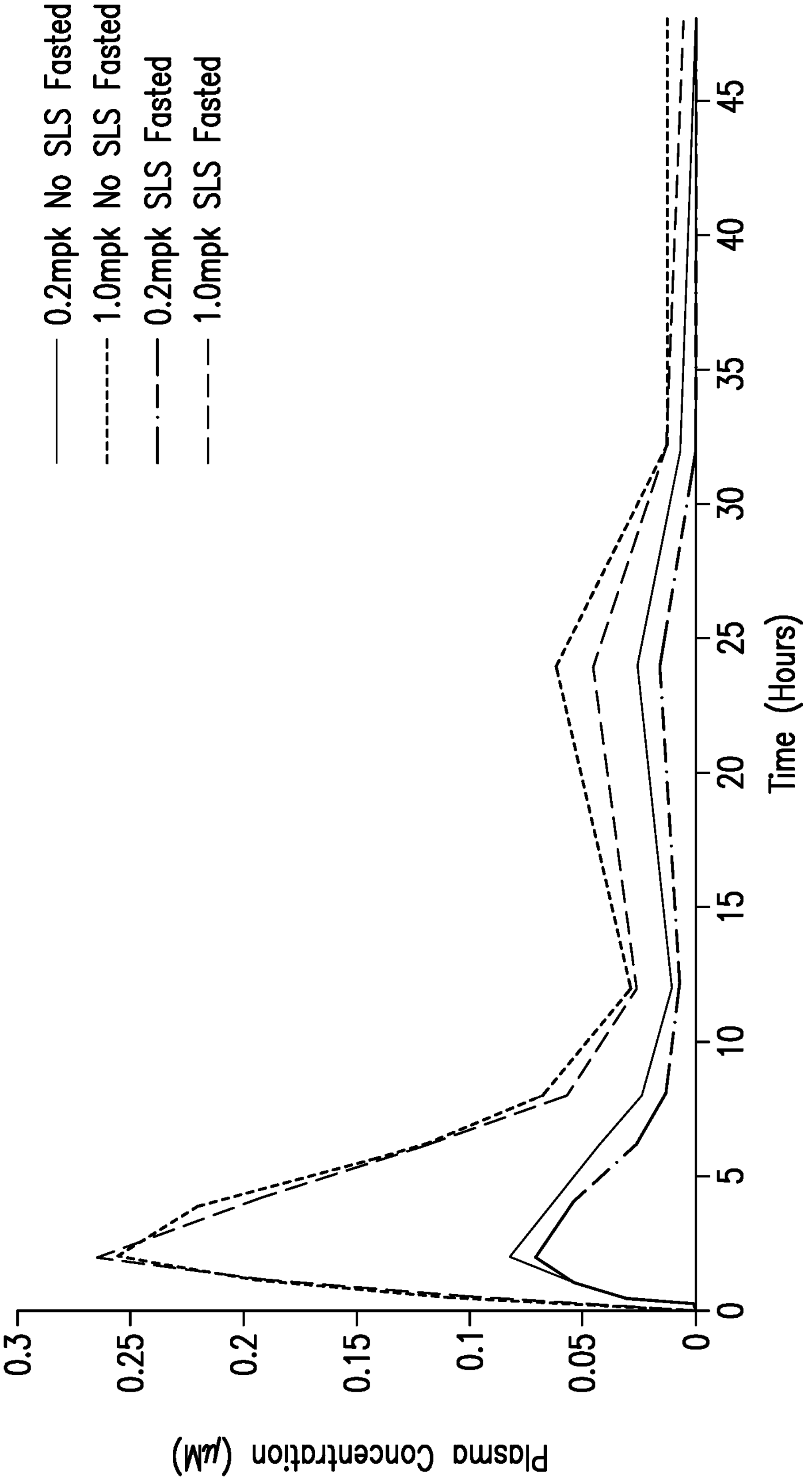
FIG. 1—Pharmacokinetic (PK) study using a sodium lauryl sulfate (SLS) surfactant FIG. 2—PK study using a TPGS surfactant FIG. 3—PK study comparing 5% w/w to 2.5% w/w and to 1% w/w TPGS

Applicants have developed a formulation of 1-[(3R,4S)-4-cyanotetrahydropyran-3-yl]-3-[(2-fluoro-6-methoxy-4-pyridyl)amino]pyrazole-4-carboxamide, the compound of Formula (I)

(I)

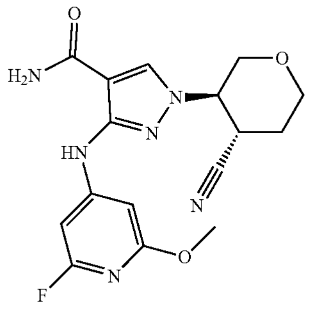

The compound of Formula (I) is a selective Janus kinase (JAK) inhibitor. However, the compound of Formula (I) is a poorly water soluble compound. Generally, poor water solubility of a pharmaceutically active agent results in poor oral bioavailability in dogs, and hence, in poor biological efficacy of the agent. Applicants have found now that the inclusion of a surfactant of an ester of a tocopherol, a polyethylene glycol (PEG) and a dicarboxylic acid in a solid pharmaceutical composition of the compound of Formula I resulted in a formulation that afforded an improved bioavailability of the compound after oral administration to an animal compared to formulations with no surfactants.

An embodiment of the invention is a solid pharmaceutical composition comprising a) a pharmaceutically effective amount of the compound of Formula (I)

Formula (I)

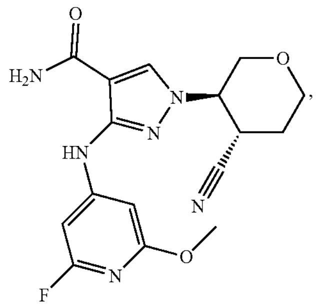

or salt or solvate thereof; and b) a pharmaceutically acceptable carrier wherein the carrier comprises a surfactant which is an ester of tocopherol, polyethylene glycol (PEG) and a dicarboxylic acid.

In an embodiment, the compound of Formula (I) is present in a crystalline form.

In an embodiment, the amount of the compound of Formula (I) in the composition is between about 0.5 and about 10% or is between about 1.0 and about 5.0% or is about 2% (w/w).

Tocopherols are a class of organic chemical compounds many of which have vitamin E activity. There are four tocopherol forms (a (alpha), P (beta), y (gamma), and 5 (delta) (see below). All feature a chromane ring, with a hydroxyl group and a hydrophobic side chain and differ by the number and position of methyl groups on the chromanol ring.

| Form | Structure |
| --- | --- |
| alpha-Tocopherol | 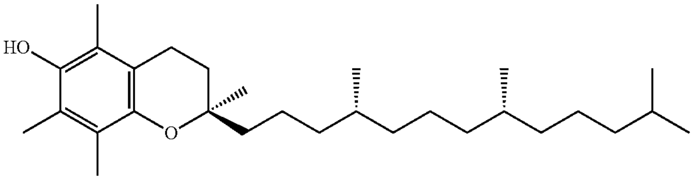 [SMILES: Cc1c(C)c2c(c(C)c1O)CC[C@@](C)(CCC[C@H](C)CCC[C@H](C)CCCC(C)C)O2] |
| beta-Tocopherol | 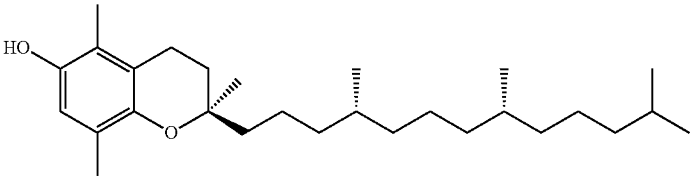 [SMILES: Cc1cc(O)c(C)c2c1O[C@](C)(CCC[C@H](C)CCC[C@H](C)CCCC(C)C)CC2] |
| gamma-Tocopherol | 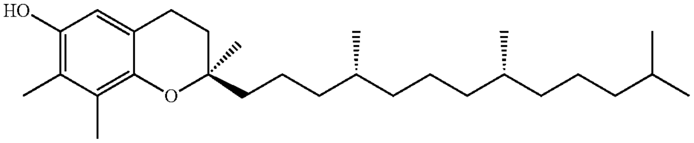 [SMILES: Cc1c(O)cc2c(c1C)O[C@](C)(CCC[C@H](C)CCC[C@H](C)CCCC(C)C)CC2] |
| delta-Tocopherol | 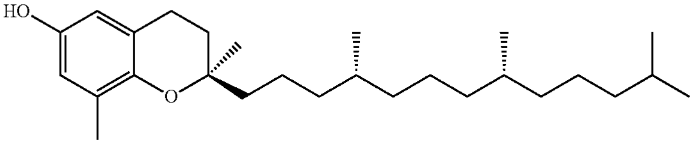 [SMILES: Cc1cc(O)cc2c1O[C@](C)(CCC[C@H](C)CCC[C@H](C)CCCC(C)C)CC2] |

In an embodiment, the tocopherol is alpha tocopherol, in particular D-alpha-tocopherol.

Polyethylene glycol is a polyether compound with a structure of H—(O—$CH_2$—$CH_2$)$_n$—OH. The molecular weight of the PEG is preferably in the range of 100 to 10,000 Da. In an embodiment, the molecular weight of the PEG is 1000 Da.

Dicarboxylic acid is an organic compound containing two carboxyl functional groups (—COOH). The general molecular formula for dicarboxylic acids can be written as $HO_2C$—R—$CO_2H$, where R can be aliphatic or aromatic. The dicarboxylic acid is preferably $C_2$-$C_{20}$ alkyl. In an embodiment, the dicarboxylic acid is succinic acid, a $C_4$ alkyl dicarboxylic acid.

In an embodiment such a surfactant is D-α-Tocopheryl polyethylene glycol 1000 succinate (TPGS or Vitamin E TPGS). TPGS is formed by the esterification of polyethylene glycol 1000 and Vitamin E succinate. Accordingly, in TPGS the molecular weight of the PEG is 1000 Da, the tocopherol is alpha tocopherol and the dicarboxylic acid is succinic acid.

In an embodiment, the amount of TPGS in the composition is between about 0.5 and about 10% or is between about 1.0 and about 5.0% or is between about 1.0% and about 2.5% (w/w).

In an embodiment, the weight ratio in the composition of the compound of Formula (I) and the TPGS is from about 0.1:1 to about 10:1, preferably about 0.5:1 to about 4:1.

The pharmaceutical composition may further contain one or more lubricants. Lubricants reduce the friction between the formed tablet and the wall of the die used to form the tablet, thus making it easier for the tablet to be removed from the die. Examples of lubricants are magnesium stearate, talc, colloidal silica, and sodium stearyl fumarate. In an embodiment, the lubricant is magnesium stearate.

The pharmaceutical composition may further contain one or more glidants. Glidants are used to improve flowability. In an embodiment, the glidant is colloidal silica, talc or mixtures thereof.

The pharmaceutical composition may further contain one or more fillers/compression aids. Fillers/compression aids are used to increase the bulk or volume of a pharmaceutical dosage form that has a low dose active ingredient and to increase the mechanical strength of a dosage form such as a tablet. Examples of fillers are microcrystalline cellulose (MCC) (Avicel PH102), lactose anhydrous, lactose monohydrate (Fast Flo 316), starch, polyols (e.g. sorbitol, mannitol, maltitol), maltodextrin, dextrose, calcium phosphate, and calcium sulphate. In an embodiment, the filler is microcrystalline cellulose, lactose monohydrate cellulose or mixtures thereof.

The pharmaceutical composition may further contain one or more disintegrants. Disintegrants help to make a tablet break into smaller pieces once in contact with a liquid. Examples of disintegrants are sodium starch glycolate, croscarmellose sodium, and crospovidone. In an embodiment, the disintegrant is sodium starch glycolate (Type A).

The pharmaceutical composition may further contain one or more binders. Binders are used to increase the mechanical strength of a dosage form such as a tablet. Binders are also used to aid granule formation in the (wet or dry) granulation process. Formation of granules increase (drug) content uniformity and flowability of the final blend. Examples of binders are PVP, hydroxypropyl methylcellulose (HPMC) and hydroxypropyl celluose (HPC). In an embodiment, the binder is hydroxypropyl celluose (HPC).

In an embodiment of the invention, the formulation is of the following composition:

| Ingredient | % (w/w) | Purpose |
|---|---|---|
| Active ingredient | 2 | Active |
| Microcrystalline Cellulose | 67.5 | Filler |
| Lactose Monohydrate | 22 | Filler |
| TPGS | 2.5 | Surfactant |
| Sodium Starch Glycolate (Type A) | 5 | Disintegrant |
| Magnesium Stearate | 1 | Lubricant |

In alternative embodiments of the invention, the concentration of the components of the formulation may vary as indicated below:

| Ingredient | % (w/w) | Purpose |
|---|---|---|
| Active ingredient | 0.5-10 | Active |
| Microcrystalline Cellulose | 0-95 | Filler |
| Lactose Monohydrate | 0-95 | Filler |
| TPGS | 0.5-10 | Surfactant |
| Sodium Starch Glycolate (Type A) | 0-10 | Disintegrant |
| Hydroxypropylcellulose | 0-5 | Binder |
| Magnesium Stearate | 0.25-1.5 | Lubricant |

In embodiment, the combined w/w percent of microcrystalline cellulose and lactose monohydrate must be at least 60%.

In embodiment, the pharmaceutical composition is a solid, preferably a capsule or a tablet.

Processes to Make the TPGS Formulations

TPGS is a waxy material and can be challenging to add to a powder blend. In practice, TPGS can be added to powder blends as either a molten liquid or aqueous solution in either a high shear granulator or hot melt extruder.

In a wet granulation process, smaller particles are bound together to form granules using a granulating fluid such as water or binder solutions. Examples of wet granulation processes are fluid bed granulation and high shear wet granulation.

In a high shear granulator, an aqueous TPGS solution or TPGS-binder solution is sprayed onto the solid components in the formulation with exception of the lubricant. The wet mass is subsequently dried for removal of water to obtain dry granules. The granules are milled and blended with a lubricant. Extragranular excipients such as filler and disintegrant may also be added prior to lubrication. The resulted lubricated blend is compressed into tablets.

Alternatively, TPGS may be heated to a molten state and be incorporated in the formulation using a high shear granulator or hot melt extruder. Granules composed of active, filler, disintegrant and TPGS will be cooled to room temperature but no water removal is necessary. Similar to wet granulation, the granules may then be milled and blended with a lubricant prior to compression. Extragranular excipients such as filler and disintegrant may also be added prior to lubrication.

Granules may be dried in fluid bed or tray dried independent of scale. Fluid bed drying would be more efficient than tray drying. The use of either method is contemplated in the context of preparing the inventive pharmaceutical compositions.

TPGS solution concentration is determined based on the TPGS concentration desired in the final pharmaceutical composition. The lower the desired concentration of TPGS in the final formulation, the more dilute the TPGS solution can be. The concentration of the TPGS solution is determined based on the desired TPGS content in the formulation and the amount of granulation liquid required to produce granules with desired attributes for downstream processing.

An embodiment of the invention is a process to make the pharmaceutical composition comprising i) forming a powder blend of the compound of Formula (I) with a filler and a disintegrant;

ii) spraying the dry powder with an aqueous TPGS solution and mixing to combine the solution with the powder;

iii) drying the product of step ii) to produce granules;

iv) size reducing the granules;

v) lubricating the product of step iv); and vi) compressing the product of step v) into a tablet to produce the pharmaceutical composition.

In an embodiment, the forming of the powder blend of step i) or the mixing of step ii) are accomplished with a high shear granulator.

An alternative embodiment of the invention is process to make the pharmaceutical composition comprising i) Forming a powder blend of the compound of Formula (I) with filler and disintegrant and heating this powder blend;
ii) melting TPGS and combining it with the heated powder blend of step i);
iii) cooling the product of step ii) to produce granules; and
iv) size reducing the granules of step iii)
v) lubricating the product of step iv); and
vi) compressing the product of step v) into a tablet to produce the pharmaceutical composition.

In an embodiment, the compound of Formula (I) is further combined with a binder in step i).

In an embodiment, the filler is microcrystalline cellulose, a lactose or mixtures thereof.

In an embodiment, the disintegrant is sodium starch glycolate.

In an embodiment, the lubricant is magnesium stearate.

In an embodiment, the binder is hydroxypropylene cellulose.

Methods of Treatment

An embodiment of the invention is a method of treating atopic dermatitis comprising administering to an animal in need thereof, an effective amount of the pharmaceutical composition of the compound of Formula (I)

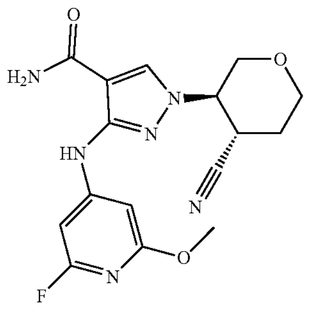 [SMILES: COc1cc(Nc2nn([C@H]3COCC[C@@H]3C#N)cc2C(N)=O)cc(F)n1]

Formula (I), or salt or solvate thereof; and a pharmaceutically acceptable carrier wherein the carrier comprises a surfactant which is an ester of tocopherol, polyethylene glycol (PEG) and a dicarboxylic acid.

A method of treating atopic dermatitis comprising administering to an animal in need thereof the pharmaceutical composition of the compound of Formula (I)

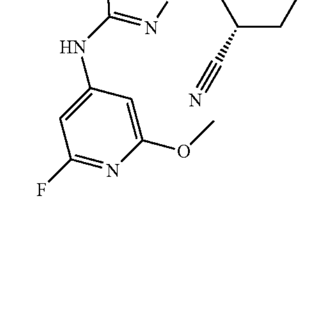

Formula (I), or salt or solvate thereof; and a pharmaceutically acceptable carrier wherein the carrier comprises a surfactant which is an ester of tocopherol, polyethylene glycol (PEG) and a dicarboxylic acid, wherein the effective amount of the compound of Formula (I) is between about 0.1 and about 2.0 mg/kg body weight.

The pharmaceutical composition is administered orally.

In an embodiment, the animal to be treated is a companion animal mammal. In another embodiment, the companion animal is a dog, a cat or a horse. In another embodiment, the companion animal is a dog.

In an embodiment of the invention, the dose of the active ingredient administered to the animal is from about 0.1 mg/kg to about 2.0 mg/kg, about 0.2 to about 0.8 mg/kg, about 0.3 to about 0.7 mg/kg, about 0.5 mg/kg, about 1.0 mg/kg.

In an embodiment, the pharmaceutical composition is administered once a day for 28 days.

In another embodiment, the pharmaceutical composition is administered twice a day for 14 days, followed by once a day for 14 days.

In other embodiment, the administration of the pharmaceutical composition is administered daily beyond the aforementioned dosing regimens as long as medically necessary including for the life of the animal.

In an embodiment, the pharmaceutical composition is administered once a day as long as medically necessary including for the life of the animal.

In an embodiment, the pharmaceutical composition is administered twice a day for up to 14 days, followed by once a day as long as medically necessary including for the life of the animal.

In an embodiment, the pharmaceutical composition is administered twice a day for one day, two days, three days, four days, five days, six days, seven days, eight days, nine days, ten days, eleven days, twelve days or thirteen days, followed by once a day as long as medically necessary including for the life of the animal.

The pharmaceutical composition of the compound of Formula (I) and TPGS may be administered in combination with antihistamines, antibiotics, antipruritics, and ceramides. These combinations may be administered simultaneously or sequentially.

EXAMPLES

Example 1—Surfactant Selection and Comparative Examples

To increase solubility of the compound and promote increase bioavailability, a number of surfactants were screened. The table below lists the solubilities of 1-[(3R,4S)-4-cyanotetrahydropyran-3-yl]-3-[(2-fluoro-6-methoxy-4-pyridyl)amino]pyrazole-4-carboxamide in the tested surfactant solutions.

| Surfactant Solution | Solubility (mg/mL) |
|---|---|
| Water | 0.008 |
| 1% sodium lauryl sulfate (SLS) | 0.1952 |
| 1% polysorbate(Tween 80) | 0.0503 |
| 10% Poloxamer 124 | 0.1081 |
| 10% Poloxamer 188 | 0.1091 |
| 10% polyvinylpyrrolidone (PVP) | 0.1327 |

-continued

| Surfactant Solution | Solubility (mg/mL) |
|---|---|
| 10% hydrogenated castor oil (RH40) | 0.4886 |
| 10% polyoxyethylated 12-hydroxystearic acid (Solutol HS 15) | 0.4595 |
| 30% HS15 | 1.4216 |
| 10% P407 | 0.2166 |
| 1% D-a-Tocopheryl polyethylene glycol 1000 succinate (TPGS) | 0.099 |
| 10% ELP | 0.5414 |
| Oleoyl macrogol-6 / polyoxyl-6 glycerides (Labrafil M1944CS) | 0.8072 |

Due to the strong solubilization of 1-[(3R,4S)-4-cyano-tetrahydropyran-3-yl]-3-[(2-fluoro-6-methoxy-4-pyridyl) amino]pyrazole-4-carboxamide by SLS and its ability to be easily incorporated into powder blends, a pharmacokinetic (PK) study was conducted with 3% w/w SLS added to the formulation. Compositions of the formulations tested containing 1% active ingredient are given below. Formulations tested containing 0.2% active ingredient were also prepared.

| Formulation with SLS | | |
|---|---|---|
| Ingredient | % (w/w) | Purpose |
| Active ingredient | 1 | Active |
| Microcrystalline Cellulose | 45 | Filler |
| Lactose Monohydrate | 45 | Filler |
| Sodium Lauryl Sulfate | 3 | Surfactant |
| Sodium Starch Glycolate (Type A) | 5 | Disintegrant |
| Magnesium Stearate | 1 | Lubricant |

| Formulation without SLS | | |
|---|---|---|
| Ingredient | % (w/w) | Purpose |
| Active ingredient | 1 | Active |
| Microcrystalline Cellulose | 48 | Filler |
| Lactose Monohydrate | 45 | Filler |
| Sodium Lauryl Sulfate | 0 | Surfactant |
| Sodium Starch Glycolate (Type A) | 5 | Disintegrant |
| Magnesium Stearate | 1 | Lubricant |

The results in FIG. 1 demonstrate that the addition of SLS was not successful in promoting increased bioavailability of the compound at two different doses despite the favorable in vitro solubility. The bioavailability of the formulations containing SLS were not improved when compared to the bioavailability of the formulations not containing SLS. For the SLS containing formulations and the non SLS formulations, the Cmax were less than 0.1 μM for the 0.2 mg/kg dose of the compound of Formula (I) and around 0.26 μM for the 1.0 mg/kg dose of the compound of Formula (I). See FIG. 1. No significant difference was show between the SLS formulations and the non-SLS formulations.

TPGS Containing Formulations

Example 2

A formulation with 4% active ingredient (API) and 5% TPGS was prepared by wet granulation. 34 g of 15% w/w TPGS aqueous solution sprayed onto approximately 90 g of powder blend containing 4 g of API. Water was removed by tray drying in a 40° C. oven overnight. Granules were milled and blended with approximately 1 g of magnesium stearate. Magnesium stearate weight was adjusted maintain 1% w/w of the final blend.

| Ingredient | % (w/w) |
|---|---|
| Active ingredient | 4 |
| Avicel PH101 (Microcrystalline cellulose-filler) | 63.75 |
| Granulac 200 (lactose monohydrate-filler) | 21.25 |
| TPGS | 5 |
| Sodium Starch Glycolate (Type A) (Disintegrant) | 5 |
| Magnesium Stearate (Lubricant) | 1 |

The following TPGS formulations were prepared as above. When a binder was added, the MCC and lactose concentration were decreased so that all components compositions added up 99%. MCC to lactose ratio was maintained at a 3:1 weight ratio. Mg stearate was added after granulation to obtain a 1% w/w concentration.

Example 3 (2% Active Ingredient, 2.5% TPGS Melt Granulation)

TPGS is pre-melted in an oven. All remaining solids in the formulation with exception of magnesium stearate was preheated. 2.5 g of molten TPGS were added to approximately 95 g of powder blend containing 2 g of API. Air cooled to RT on a tray under ambient conditions. The granules were milled and then blended with approximately 1 g of magnesium stearate. Magnesium stearate weight was adjusted to maintain 1% w/w of the final blend.

Example 4—Bioavailability of TPGS Containing Formulations in Dogs

TPGS was assessed as a surfactant to promote increased bioavailability of the active ingredient, 1-[(3R,4S)-4-cyano-tetrahydropyran-3-yl]-3-[(2-fluoro-6-methoxy-4-pyridyl) amino]pyrazole-4-carboxamide in dogs. Formulations were prepared as described above. The compositions of the formulation is given below:

| Ingredient | % (w/w) |
|---|---|
| Active ingredient | 0.5-10 |
| Microcrystalline cellulose | 67.5 |
| Lactose monohydrate | 22 |
| TPGS | 2.5 |
| Sodium Starch Glycolate (Type A) | 5 |
| Magnesium Stearate | 1 |

The percentage of the microcrystalline cellulose and lactose monohydrate were adjusted slightly to accommodate the change in concentration of the active ingredient.

Figure 2:
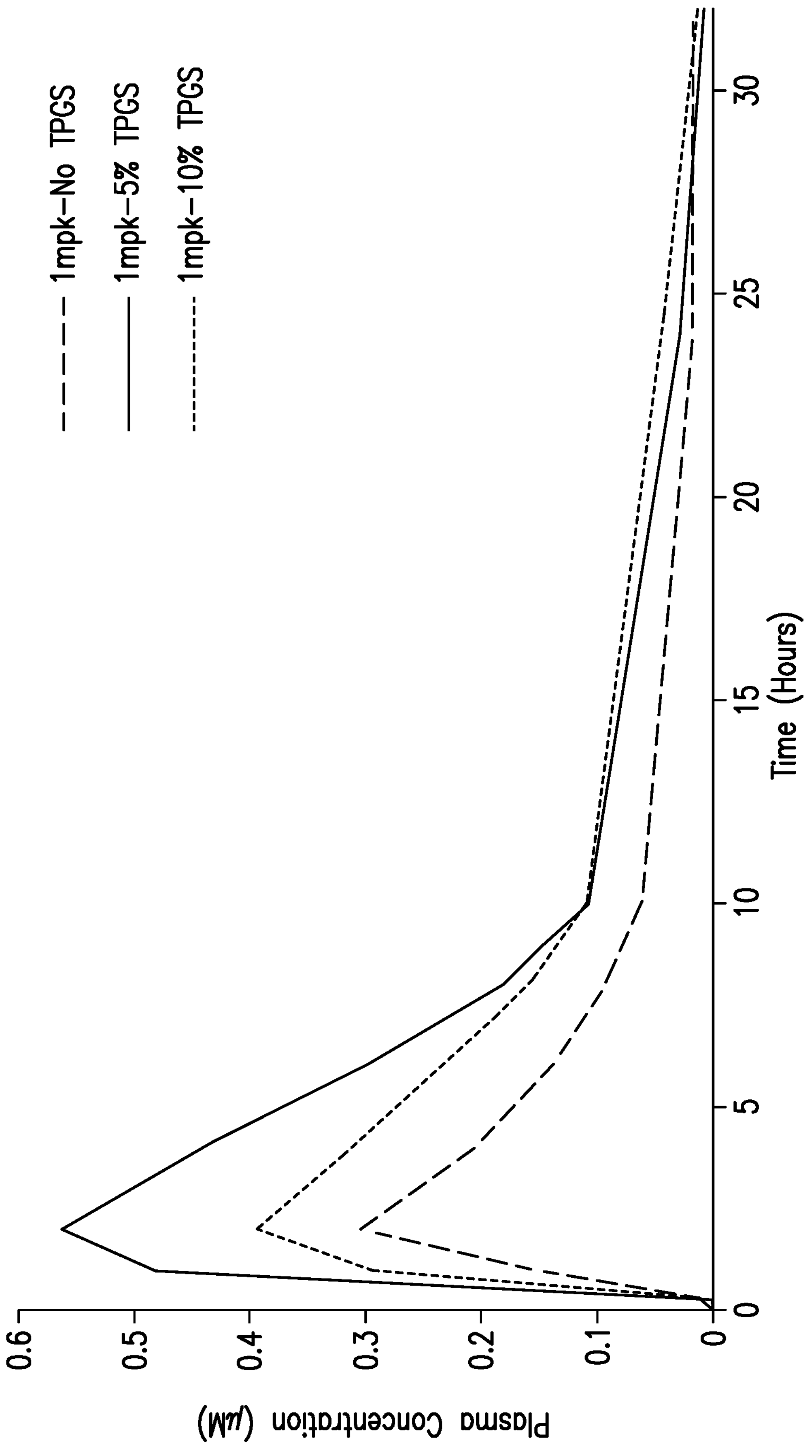

The bioavailability of the compound of Formula (I) in dogs was assessed for range of TPGS formulations from 1% to 10% TPGS w/w. All formulations were dosed at 1 mg/kg of body weight. FIG. 2 shows the data comparing the pharmacokinetic (PK) profile when the compound was formulated with 10% w/w TPGS, 5% w/w TPGS, and no TPGS. The Cmax for the formulation that did not contain TPGS was measured at about 0.3 μM. The Cmax of the 5%

TPGS formulation and the 10% formulation were about 0.6 μM and 0.4 μM respectively. See FIG. 2.

Figure 3:
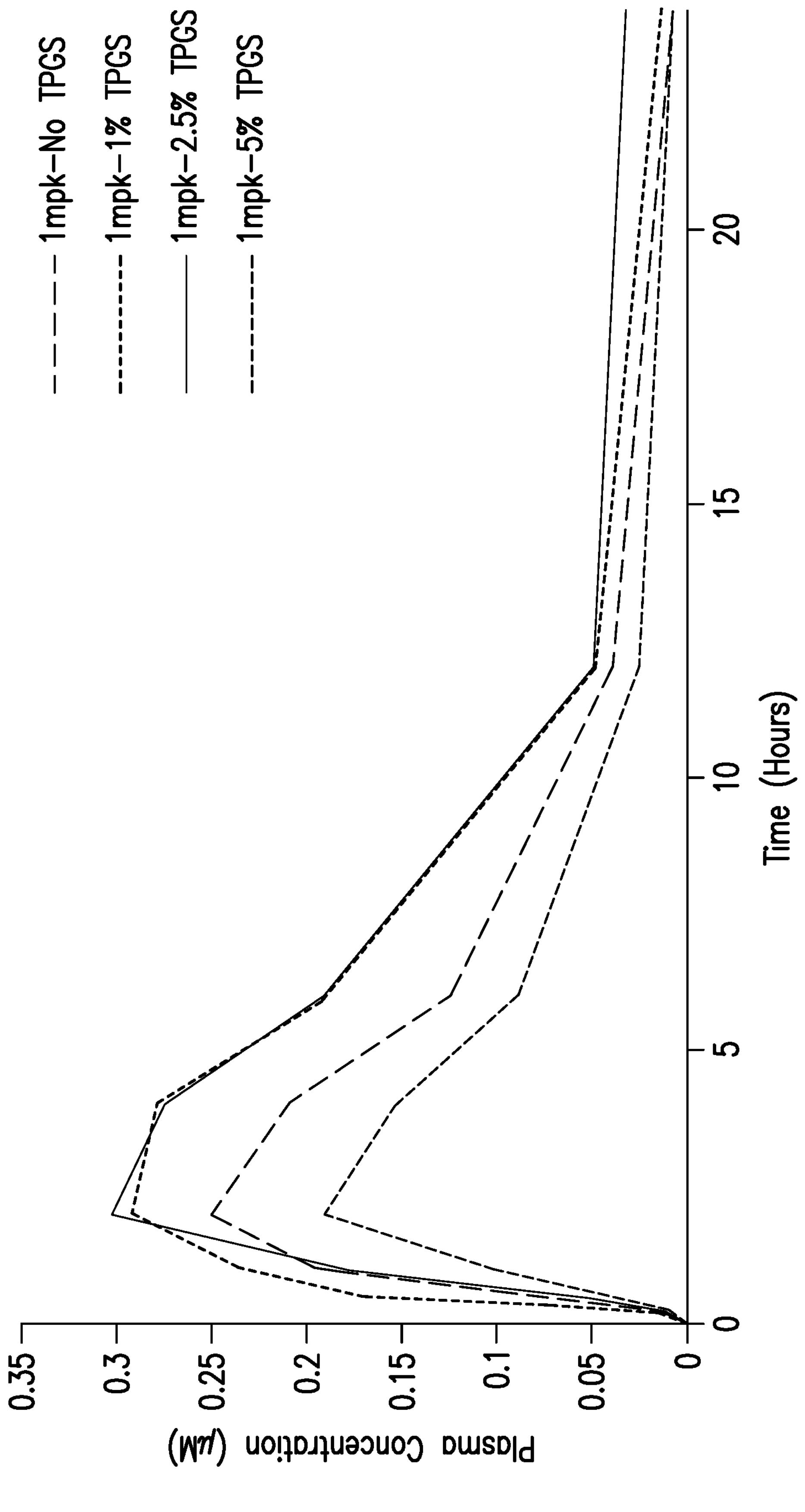

These results demonstrated that while inclusion of TPGS is important for promoting bioavailability, a reduced concentration of TPGS may be beneficial. Therefore, a follow-up study comparing 5% w/w to 2.5% w/w and to 1% w/w TPGS was conducted. The results are shown in FIG. 3. In this study, the Cmax of the formulation that did not contain TPGS was measured at about 0.2 μM. The Cmax of the 1%, 2.5% and 5% TPGS formulations were about 0.3 μM, 0.3 μM and 0.25 μM respectively. See FIG. 3. Again, here the data demonstrated that a lower concentration of TPGS improved bioavailability. Due to variations between study sites, it is not possible to directly compare the data of FIGS. 2 and 3 to each other or to the data of FIG. 1. However, in both TPGS studies, the TPGS containing formulations had greater bioavailability than the formulations with no TPGS. This was unexpected given the results of the bioavailability studies with SLS where despite its much greater solubility for the compound of Formula (I), the SLS formulations produced no improvement of bioavailability of the compound of Formula (I) over the formulations with no SLS. At 1% concentration, SLS has a solubility of the compound of Formula (I) of 0.1952 mg/mL and at 1% concentration, TPGS has a solubility of the compound of Formula (I) of 0.099. mg/mL Example 6 (3% Active, 3.5% TPGS)

A formulation with 3% active ingredient (API) and 3.75% TPGS was prepared by high shear wet granulation. A solution containing 11% w/w TPGS and 15% polyvinylpyrrolidone was sprayed onto approximately 2 kg of powder blend containing 3% w/w API. Wet granules were dried in a fluid bed dryer until loss on drying is s 2.5%. Dried granules were milled and blended with approximately additional sodium starch glycolate type A and magnesium stearate. Extragranularly added sodium starch glycolate Type A weight was adjusted to maintain 3% w/w of the final blend. Magnesium stearate weight was adjusted to maintain 0.5% w/w of the final blend.

| Ingredient | % (w/w) | Purpose |
|---|---|---|
| Active ingredient | 3.00 | Active |
| Microcrystalline Cellulose | 53.17 | Filler |
| Lactose Monohydrate | 26.58 | Filler |
| TPGS | 3.75 | Surfactant |
| Sodium Starch Glycolate (Type A) | 8.00 | Disintegrant |
| Polyvinylpyrrolidone | 5.00 | Binder |
| Magnesium Stearate | 0.50 | Lubricant |

Example 7

A formulation with 3% active ingredient (API) and 3.75% TPGS was prepared by high shear wet granulation. A solution containing approximately 10% w/w TPGS was sprayed onto approximately 2 kg of powder blend containing 3% w/w API. Wet granules were dried in a fluid bed dryer until loss on drying is ≤2.5%. Dried granules were milled and blended with approximately additional sodium starch glycolate type A and magnesium stearate. Extragranularly added sodium starch glycolate Type A weight was adjusted to maintain 3% w/w of the final blend. Magnesium stearate weight was adjusted to maintain 0.5% w/w of the final blend.

| Ingredient | % (w/w) | Purpose |
|---|---|---|
| Active ingredient | 3.00 | Active |
| Microcrystalline Cellulose | 54.17 | Filler |
| Lactose Monohydrate | 27.08 | Filler |
| TPGS | 3.75 | Surfactant |
| Sodium Starch Glycolate (Type A) | 8.00 | Disintegrant |
| Hydroxypropyl cellulose | 3.00 | Binder |
| Magnesium Stearate | 0.50 | Lubricant |

Example 8—Efficacy Study

The compound is being evaluated in a masked and randomized proof-of-concept study in dogs with a diagnosis of atopic dermatitis. The objective of this study is to evaluate the efficacy and tolerability of the compound against atopic dermatitis in client-owned dogs. The compound will be evaluated at two doses and will be compared to a placebo control. Dogs will be dosed orally twice daily for up to 14 days followed by once daily for up to 28 days, or once daily for 28 days, and will be evaluated for pruritus and skin lesions using the Pruritus Visual Analog Scale (PVAS) and Canine Atopic Dermatitis Extent and Severity Index (CADESI-4) scoring tools, respectively.

The Canine Atopic Dermatitis Extent and Severity Index (CADESI-4) is a severity scale used to grade skin lesions in clinical trials for treatment of dogs with atopic dermatitis (AD). Three lesion types (erythema, lichenification and alopecia/excoriation) are scored from 0 to 3 at each of 20 body sites, for a maximal score of 180, with proposed benchmarks for mild, moderate and severe AD skin lesions of 10, 35 and 60, respectively. CADESI-4: Thierry, O., Manolis, S., Nuttall, T., Bensignor, E., Griffin, C., Hill, P., for the International Committee on Allergic Diseases of Animals (ICADA). Validation of the Canine Atopic Dermatitis Extent and Severity Index (CADESI)-4, a simplified severity scale for assessing skin lesions of atopic dermatitis in dogs. Vet, Dermatol. 25:77-e25, 2014

The Pruritus Visual Analog Scale (PVAS) is a visual analog scale that contains features of both the severity of itching and behaviors associated with itching. It is commonly used to determine the severity of pruritus in clinical trials for treatment of dogs with AD. PVAS: Hill, P. B., Lau, P., and Rybnicek, J. Development of an owner-assessed scale to measure the severity of pruritus in dogs. Vet. Dermatol. 18:301-308, 2007.

The invention claimed is:

1. A solid pharmaceutical composition comprising a) a pharmaceutically effective amount of the compound of Formula (I)

Formula (I)

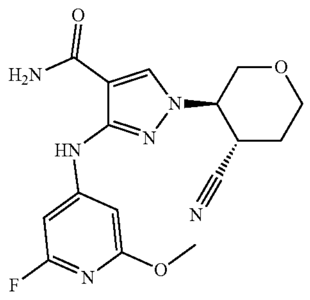

or salt or solvate thereof; and b) a pharmaceutically acceptable carrier wherein the carrier comprises a surfactant which is an ester of tocopherol, polyethylene glycol (PEG) and a dicarboxylic acid.

2. The pharmaceutical composition of claim 1, wherein the tocopherol is alpha tocopherol, the molecular weight of the PEG is between 100 and 10, 000 Da and the dicarboxylic acid is of the formula HO2C—R—CO2H, where R is C2-C20 alkyl.

3. The pharmaceutical composition of claim 1, wherein the carrier comprises D-α-Tocopheryl polyethylene glycol 1000 succinate (TPGS).

4. The pharmaceutical composition of claim 1, wherein the compound of Formula (I) is present in a crystalline form.

5. The pharmaceutical composition of claim 1, wherein the amount of the compound of Formula (I) in the composition is between about 0.5 and about 10% or is between about 1.0 and about 5.0% or is about 2% (w/w).

6. The pharmaceutical composition of claim 3, wherein the amount of TPGS in the composition is between about 0.5 and about 10% or is between about 1.0 and about 5.0% or is between about 1.0% and about 2.5% (w/w).

7. The pharmaceutical composition of claim 1, further comprising one or more excipients selected from, a filler, a lubricant, a binder and a disintegrant.

8. The pharmaceutical composition of claim 7, wherein the filler is a microcrystalline cellulose, a lactose or mixtures thereof.

9. The pharmaceutical composition of claim 7, wherein the lubricant is magnesium stearate.

10. The pharmaceutical composition of claim 7, wherein the disintegrant is sodium starch glycolate.

11. The pharmaceutical composition of claim 7, wherein the binder is hydroxypropyl cellulose.

12. A method of treating atopic dermatitis comprising administering to an animal in need thereof, an effective amount of the pharmaceutical composition of claim 1.

13. The method of claim 12, wherein the effective amount of the compound of Formula (I) is between about 0.1 and about 2.0 mg/kg body weight.

14. The method of claim 12, wherein the animal is a dog.

15. The method of claim 12, wherein the composition is administered once per day or twice per day.

16. The method of claim 12, wherein the composition is administered with food.

17. The method of claim 12, wherein the composition is administered twice a day for 14 days and then once a day for 14 days.

18. The method of claim 12, wherein the composition is administered once a day for 28 days.

19. A process to make the pharmaceutical composition of claim 3 comprising i) forming a powder blend of the compound of Formula (I) with a filler and a disintegrant;

ii) spraying the dry powder with an aqueous TPGS solution and mixing to combine the solution with the powder;

iii) drying the product of step ii) to produce granules;

iv) size reducing the granules;

v) lubricating the product of step iv); and vi) compressing the product of step v) into a tablet to produce the pharmaceutical composition.

20. The process of claim 19, wherein the forming of the powder blend of step i) or the mixing of step ii) are accomplished with a high shear granulator.

21. A process to make the pharmaceutical composition of claim 3 comprising i) Forming a powder blend of the compound of Formula (I) with filler and disintegrant and heating this powder blend;

ii) melting TPGS and combining it with the heated powder blend of step i);

iii) cooling the product of step ii) to produce granules; and iv) size reducing the granules of step iii)

v) lubricating the product of step iv); and vi) compressing the product of step v) into a tablet to produce the pharmaceutical composition.

22. The process of claim 19, wherein the compound of Formula (I) is further combined with a binder in step i).

23. The process of claim 21, wherein the compound of Formula (I) is further combined with a binder in step i).

24. The pharmaceutical composition of claim 1, wherein the dicarboxylic acid is succinic acid.

25. A solid pharmaceutical composition comprising a) 0.5-10% w/w of the compound of Formula (I)

Formula (I)

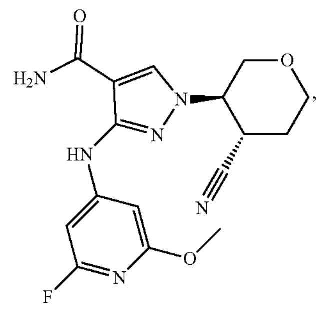

or salt or solvate thereof;

b) 0-95% w/w of microcrystalline cellulose;

c) 0-95% w/w of lactose monohydrate;

d) 0.5-10% w/w of D-α-Tocopheryl polyethylene glycol 1000 succinate (TPGS);

e) 0-10 5 w/w of sodium starch glycolate;

d) 0-5% w/w of hydroxypropylcellulose; and e) 0.25-1.5 of magnesium stearate.

* * * * *